United States Patent [19]

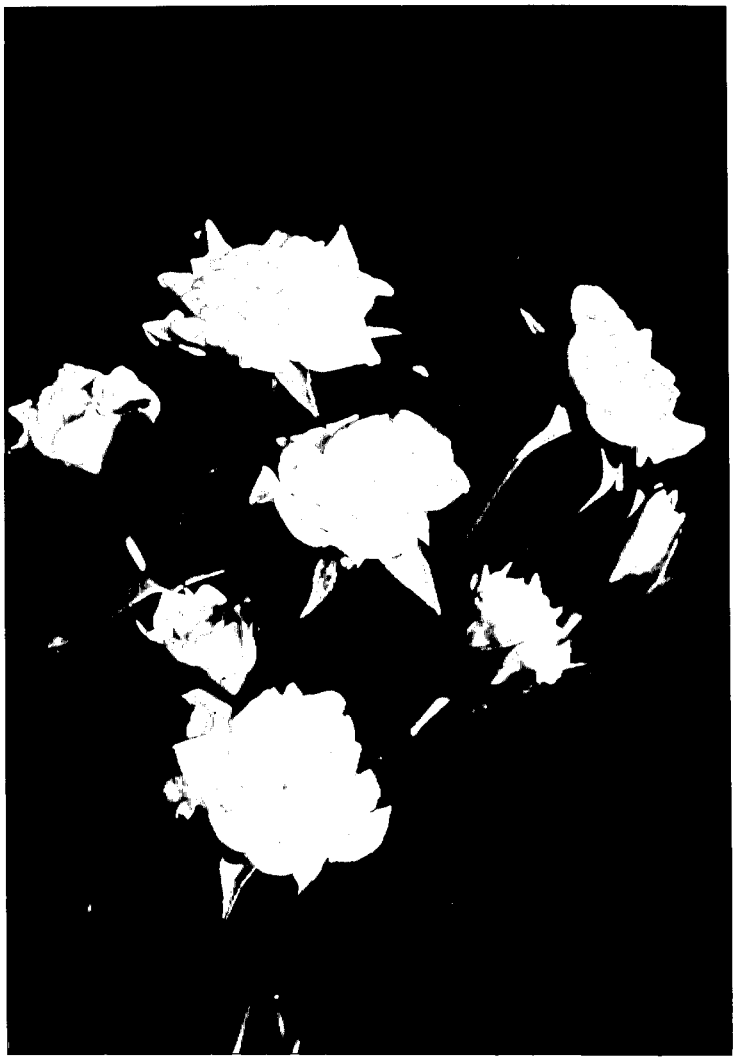

Moore

[11] Patent Number: Plant 5,791

[45] Date of Patent: Oct. 21, 1986

[54] ROSE PLANT/VAR. MORQUAKE

[75] Inventor: Ralph S. Moore, Visalia, Calif.

[73] Assignee: Sequoia Nursery, Visalia, Calif.

[21] Appl. No.: 668,251

[22] Filed: Nov. 5, 1984

[51] Int. Cl.[4] ..... A01H 5/00

[52] U.S. Cl. ..... Plt./7

[58] Field of Search ..... Plt./7

*Primary Examiner*—Robert E. Bagwill

[57] ABSTRACT

This invention relates to a new and distinct variety of miniature rose plant primarily identified by its many petaled (double) flowers which are striped, or varigated in varying patterns of red and yellow.

1 Drawing Figure

The present invention relates to a new and distinct variety of hardy, dwarf, bush type rose plant of the miniature class; the variety being primarily characterized — as to novelty — by the buds and flowers which are striped (or varigated) in varying patterns of red and yellow.

The variety is further characterized by:

An abundance of bloom, with flowers usually borne singly, but also several to the stem in loose clusters.

Some fragrance.

A plant which is vigorous, of rounded, upright shape with small semi-glossy foliage with pointed leaflets; the buds and flowers being similar in form and size to Golden Angel (miniature—U.S. Plant Pat. No. 4,028).

The plant, which has a normal height of 14–18 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Golden Angel (U.S. Plant Pat. No. 4,028 — miniature) as the seed parent and an un-named striped seedling (Dortmund × un-named striped seedling miniature) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; upright; seeding; greenhouse; outdoors; cut flowers; garden decoration; potted plant.

*Variety identification.*—MORquake (Commercial synonym: EARTHQUAKE).

Flowers borne: Singly and several together (3 to 5) on slender wirey stems.

Quantity of bloom: Abundant both outside and in greenhouse.

Bud:

*Peduncle.*—Medium length; slender but sturdy; erect; medium to light green, sometimes tinted bronze (outdoors); with numerous soft prickles and few or no short hairs.

*Before calyx breaks.*—Size — small. Form ovoid to pointed with several foliaceous apendages on surface of bud: with foliaceous parts extending beyond the tip of the bud equal to one-half or more of its length. Color — medium green, occasionally tinted with bronze (outdoors).

*As calyx breaks.*—Color — may vary from red to yellow (sometimes near white) with some buds being red on one side and yellow (even striped) on the other. Opening — opens well in all weather.

Bloom:

*Size when fully open.*—Small, averaging about 35 mm ($1\frac{1}{2}''$).

*Petalage.*—Double — averaging about 45–55 petals (sometimes more), arranged regularly plus several small petaloids.

*Form.*—High centered with petals rolled loosely outward and downward. Open flowers usually show few or no stamens.

Petals: Fairly thick; satiny on inside and on outside surface.

*Shape.*—Outside petals, broad lanceolate with rounded or small acute tip; intermediate — broad lanceolate with small acute tip; inside — lanceolate with acute tip.

Color: Newly opened flower from a plant grown in plastic greenhouse (August 1984), Visalia, Calif.:

*Outside petal.*—Outside surface — basically yellow — near Canary Yellow 4/2, but may be both lighter and deeper yellow on same petal (or flower). This basic yellow color may be blended with red or may show red coloring from color on upper surface bleeding through to the yellow of lower surface. Also red and yellow color pattern on this (outside) surface may be different from similar areas on upper (inside) surface. Inside surface — basically yellow — near Canary Yellow 4/2, or lighter, shading into near Canary Yellow 4/1 at base and overlaid, blended or striped with red which may vary from a shade near Orient Red 819/3 to red of a shade similar to Currant Red 821/2 or Currant Red 821/1. This red color is modified in varying degrees by (1) the yellow under color. (2) by blackish shading in the basic red and (3) by minute flecking and interaction of the red and yellow color. Age of flower, weather and light intensity can also affect both the red and yellow colors.

*Intermediate petal.*—Outside surface similar to outside petal. Inside surface similar to outside petal.

*Inner petal.*—Outside surface — same as intermediate petal; inside surface — same as intermediate petal. General color effect; buds and newly opened flowers — a varigated red and yellow color pattern with no two flowers alike. Three days open — color — similar to newly opened flowers, but lighter color — the red areas becoming more pink and the yellow areas becoming lighter yellow to cream. Behavior — opens well in all weather. Spent petals drop off. Flower longevity (August 1984) — plant in pot 4–6 days or longer. Cut flowers at living room temperature 4–5 days or longer.

Reproductive organs:

*Stamens.*—When present: arranged regularly about pistils.

*Filaments.*—Varying length, short, yellow.

*Anthers.*—Few or none; yellow.

*Pollen.*—Small amount.

*Pistils.*—Average number.

*Styles.*—Varying length — fairly short; yellowish; bunched; often malformed.

*Ovaries.*—All enclosed in calyx.

*Hips.*—None.

*Sepals.*—Permanent; spear shaped; recurved.

*Seed.*—None.

Foliage.

*Leaves.*—Compound of five (somtimes three or seven) leaflets; medium small; leathery; semi-glossy.

*Leaflets.*—Shape: broad, lanceolate; apec acute; base rounded — sometimes acute. Color: medium green; new growth — normal (medium) green (sometimes tinted reddish). Rachis: medium strength; upper side usually few or no prickles or hairs; grooved; underside may have several thorns (1 to 3) and few or no tiny prickles or hairs. Stipules: medium to short length; medium width; short to medium length narrow points which turn out usually at about 45 degrees or more.

Growth:

*Habit.*—Dwarf; bushy; upright; much branched.

*Growth.*—Free vigorous; internodes short.

*Canes.*—Medium; slender; sturdy.

*Main stems.*—Color; medium green.

*Thorns.*—Several; inclined or curved slightly downward. Prickles — none. Hairs — none.

*Branches.*—Color: medium green. Thorns: several; slender; inclined slightly downward. Prickles — none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, substantially as illustrated and described, characterized by buds and flowers having many petals (45 or more) and uniquely striped in shades of red and yellow, and further characterized by a plant of compact well rounded shape, vigorous, with the main stems and shoots being moderately thorny, the said plant being easy to propagate from cuttings or by budding, with an abundance of small semi-glossy foliage and an abundance of flowers borne singly or several to the stem in loose clusters.

* * * * *